(12) United States Patent
St. Germain et al.

(10) Patent No.: US 7,927,268 B1
(45) Date of Patent: Apr. 19, 2011

(54) COUNTERPULSATION DEVICE WITH INCREASED VOLUME-DISPLACEMENT EFFICIENCY AND METHODS OF USE

(75) Inventors: Jon P. St. Germain, Maple Grove, MN (US); Peter T. Keith, Maple Grove, MN (US); Denise R. Barbut, Maple Grove, MN (US)

(73) Assignee: CoAxia, Inc., Maple Grove, MN (US)

( * ) Notice: Subject to any disclaimer, the term of this patent is extended or adjusted under 35 U.S.C. 154(b) by 15 days.

(21) Appl. No.: 11/873,332

(22) Filed: Oct. 16, 2007

Related U.S. Application Data (62) Division of application No. 10/654,368, filed on Sep. 2, 2003, now abandoned.

(51) Int. Cl.
*A61N 1/362* (2006.01)
(52) U.S. Cl. ............................................. 600/18
(58) Field of Classification Search .......... 600/16, 600/18
See application file for complete search history.

(56) References Cited

U.S. PATENT DOCUMENTS

| | | |
|---|---|---|
| 3,504,662 A | 4/1970 | Jones |
| 3,692,018 A | 9/1972 | Goetz et al. |
| 3,720,200 A | 3/1973 | Laird |
| 4,077,394 A | 3/1978 | McCurdy |
| 4,601,706 A | 7/1986 | Ailon |
| 4,697,574 A | 10/1987 | Karcher et al. |
| 4,701,160 A | 10/1987 | Lindsay et al. |
| 4,798,588 A | 1/1989 | Ailon |
| 4,902,272 A | 2/1990 | Milder |
| 5,195,942 A | 3/1993 | Weil et al. |
| 5,221,258 A | 6/1993 | Shturman |
| 5,330,451 A | 7/1994 | Gabbay |
| 5,330,498 A | 7/1994 | Hill |
| 5,334,142 A | 8/1994 | Paradis |
| 5,437,633 A | 8/1995 | Manning |
| 5,449,342 A | 9/1995 | Hirose et al. |
| 5,458,574 A | 10/1995 | Machold et al. |
| 5,531,776 A | 7/1996 | Ward et al. |
| 5,599,329 A | 2/1997 | Gabbay |

(Continued)

FOREIGN PATENT DOCUMENTS

WO    WO 99/15227    4/1999

(Continued)

OTHER PUBLICATIONS

Apostolides et al., "Intra-aortic Balloon Pump Counterpulsation in the Management of Concomitant Cerebral Vasospasm and Cardiac Failure after Subarachnold Hemorrhage: Technical Case Report"; Neurosurgery, 38:5, May 1996, pp. 1056-1060.

(Continued)

*Primary Examiner* — Mark W Bockelman
(74) *Attorney, Agent, or Firm* — O'Melveny & Myers LLP (57) ABSTRACT

A method for mechanically assisting the pumping action of the heart. A catheter is provided comprising an elongate member having a proximal end, a distal region, an expandable member attached in the distal region, and an inflatable member in the distal region and attached distal the expandable member. The catheter is advanced into the aorta. The expandable member is expanded to at least partially obstruct the aorta. The inflatable member is inflated during diastole. The inflatable member is then deflated during the ejection phase of the left ventricle while expansion of the expandable member is maintained. The pumping action of the heart is thereby mechanically assisted. Cerebral perfusion augmentation may also be achieved by use of combined coarctation-counterpulsation devices and methods. Devices for practicing methods with increased volume-displacement efficiency are also described.

14 Claims, 12 Drawing Sheets

U.S. PATENT DOCUMENTS

| | | | |
|---|---|---|---|
| 5,662,671 | A | 9/1997 | Barbut et al. |
| 5,678,570 | A | 10/1997 | Manning |
| 5,702,368 | A | 12/1997 | Stevens et al. |
| 5,711,754 | A | 1/1998 | Miyata et al. |
| 5,716,386 | A | 2/1998 | Ward et al. |
| 5,814,016 | A | 9/1998 | Valley et al. |
| 5,820,593 | A | 10/1998 | Safar |
| 5,827,237 | A | 10/1998 | Mocoviak |
| 5,855,210 | A | 1/1999 | Sterman et al. |
| 5,891,012 | A | 4/1999 | Downey et al. |
| 6,010,522 | A | 1/2000 | Barbut et al. |
| 6,190,304 | B1 | 2/2001 | Downey et al. |
| 6,296,654 | B1 | 10/2001 | Ward |

FOREIGN PATENT DOCUMENTS

| | | |
|---|---|---|
| WO | WO 99/30765 | 6/1999 |
| WO | WO 99/58174 | 11/1999 |

OTHER PUBLICATIONS

Bhayana et al., "Effects of Intraaortic Balloon Pumping on Organ Perfusion in Cardiogenic Shock;" Journal of Surgical Research, 26(2):108-113 (1979).

Boston, et al., "Differential: A New Technique for Isolated Brain Cooling During Cardiopulmonary Bypass," Ann. Thorac. Surg. 69:1346:50.

Cheung et al., Relationships Between Cerebral Blood Flow Velocities and Arterial Pressures During Intra-Aortic Counterpulsation:, Journal of Cardiothoracic and Vascular Anesthesia, 12:1, pp. 51-57, Feb. 1998.

Edmunds, Jr. et al.,"An Adjustable Pulmonary Arterial Band", Trans. Amer. Soc Artificial Internal Organs, vol. XVII, 1972, pp. 237-223.

Nanas et al., "Counterpulsation: Historical Background, Technical Improvements, Hemodynamic and Metabolic Effects," Cardiology, 84:156-167 (1994).

Nussbaum et al., "Intra-Aortic Balloon Counterpulation Augments Cerebral Blood Flow in the Patient with Cerebral Vasospasm; a Xenon-Enhanced Computed Tomograph Study," Neurosurgery, 42(1):206-14 (1998).

Nussbaum et al., "Intra-Aortic Balloon Counterpulsation Augments Cerebral Blood Flow in a Canine Model of Subarachnold Hemorrhage-Induced Cerebral Vasospasm," Neurosurgery, 36(4):879-86 (1995).

Sabiston, Textbook of Surgery, Sabiston, Ed., W.B. Saunders Company, publisher, 1981, pp. 2462-2463.

Tranmer et al., "Intra-aortic balloon counterpulsation: a treatment for ishcaemic stroke?" Neurol. Res., 11(2):109-113 (1989).

Tranmer et al., "Pulsatile Versus Nonpulsatile Blood Flow in the Treatment of Actue Cerebral Ischemia," Neurosurgery, 19(5):724-31 (1986).

COUNTERPULSATION DEVICE WITH INCREASED VOLUME-DISPLACEMENT EFFICIENCY AND METHODS OF USE

This is a divisional of U.S. application Ser. No. 10/654,368, filed Sep. 2, 2003, now abandoned which is hereby expressly incorporated by reference in its entirety.

FIELD OF THE INVENTION

The present invention relates to methods and devices for coarctation and counterpulsation for left ventricular assist and enhancement of cerebral blood flow. More particularly, the invention relates to catheters with propagating balloon inflation for intraaortic balloon pumping with increased volume-displacement efficiency.

BACKGROUND OF THE INVENTION

Despite recent advances made in diagnosing and treating cardiovascular disorders, coronary heart disease remains the leading cause of mortality in the United States. In 2001, 1.1 million Americans were expected to have a new or recurrent myocardial infarction. Approximately one third to one half of patients who experience their first myocardial infarction will die as a result of complications related to their acute event. Despite modern pharmacologic support, cardiogenic shock, defined as inadequate tissue perfusion resulting from a decline in cardiac output, is still a highly lethal complication of an acute myocardial infarction.

A variety of left ventricular assist devices have been developed to support the failing myocardium. The intraaortic balloon pump (IABP), which assists the ischemic ventricle through improving coronary perfusion and reducing systemic vascular resistance by counterpulsation, is by far the most widely used left ventricular assist device. The conventional IABP catheter comprises a central lumen for passage of a guidewire during insertion and for monitoring aortic blood pressure. A balloon made of polyurethane is mounted on the catheter and communicates with an outer lumen that provides a passageway for gas exchange and is connected to a console that synchronizes inflation and deflation with the cardiac cycle. The principal of counterpulsation works by deflating the balloon during systole, resulting in a reduction in systemic afterload and vascular resistance. The balloon is inflated during diastole resulting in an improvement of left ventricular performance through an increase in coronary perfusion and a decrease in myocardial oxygen consumption. Counterpulsation also causes an increase in peripheral blood flow.

Counterpulsation has been found to be successful in reversing the shock state in 80 to 85 percent of patients with cardiogenic shock after myocardial infarction. Counterpulsation is also very effective in the initial stabilization of patients with mechanical intracardiac defects complicating myocardial infarction, such as acute mitral regurgitation and ventricular septal defect. Other uses of counterpulsation include (1) treating patients with unstable angina, (2) weaning patients from cardiopulmonary bypass, (3) providing mechanical support for patients in heart failure while waiting for cardiac transplant, and (4) prophylactic application in patients with severe left ventricular dysfunction prior to or during surgery or percutaneous angioplasty.

At the present time, balloons on the IABP catheter for percutaneous insertion are available in 30 cc, 40 cc, and 50 cc volumes. Although the sizes and design of these balloons are somewhat successful in improving cardiac performance, a relatively large balloon size is required to accomplish adequate displacement of blood volume during its inflation, and to accomplish adequate backflow of blood volume during its deflation. Large balloon size is required because, during inflation, blood is displaced not only upstream (as intended for cardiac assist), but also downstream (unproductive for cardiac assist), and therefore a substantial volume of blood is dispersed to the peripheral vasculature. Likewise, during deflation, backflow occurs to draw blood not only from upstream (as intended to reduce afterload), but also from downstream (unproductive for cardiac assist), and therefore substantial backflow is wasted on drawing blood from the peripheral vasculature. Thus, new devices and methods are needed for increasing the displacement and backflow efficiency of the intraaortic balloon pump and counterpulsation, while decreasing balloon size.

SUMMARY OF THE INVENTION

The present invention relates to devices and methods for mechanically assisting the pumping action of the heart. In one embodiment, the device comprises a catheter comprising an elongate member having a proximal end and a distal region. The catheter further comprises an expandable member (e.g., a balloon or impermeable membrane) attached in the distal region and an inflatable member in the distal region and attached distal the expandable member. The inflatable member (e.g., a balloon) typically has a volume of between 10-30 cc. The catheter has a lumen that communicates with the inflatable member and extends proximally.

The catheter may also have a guidewire lumen. In certain cases, the catheter is further provided with a first blood pressure measuring mechanism for measuring blood pressure between the expandable member and the inflatable member, and a second blood pressure measuring mechanism for measuring blood pressure upstream the inflatable member. The pressure measuring mechanism may take the form of either a pressure lumen that communicates with an external blood pressure transducer or a blood pressure transducer mounted on the catheter.

In use, the distal end of the catheter is advanced into the aorta and typically positioned so that the expandable member and the inflatable member are within the descending aorta. The expandable member is expanded to partially obstruct (e.g., to achieve 60% or more, 70% or more, 80% or more, or 90% or more luminal obstruction) or to fully obstruct the aorta. Where the expandable member is a balloon, it can be filled with saline or a gas (e.g., carbon dioxide or helium). The expandable member may be maintained in an expanded state during systole and diastole with either complete or partial aortic obstruction. Alternatively, the expandable member is cycled between an expanded state and a contracted state. If the expandable member is cycled, then typically it will be expanded before inflating the inflatable member, and contracted after deflating the inflatable member. That is, the expandable member may be timed with the cardiac cycle as is the inflatable member. Moreover, the expandable member may be a volume displacement member in the manner of the inflatable member.

After the expandable member is expanded to at least partially obstruct the aorta, the inflatable member is inflated with a gas (e.g., carbon dioxide or helium) during diastole and deflated by withdrawing the gas during systole, i.e., the ejection phase of the left ventricle. In certain cases, the methods will include measuring an electrocardiogram and synchronizing inflation with the R wave of the electrocardiogram, so that maximum inflation occurs at the peak of the T wave (which corresponds approximately with closure of the aortic valve), and deflation is timed to occur just before the next QRS complex of the electrocardiogram (which correlates with ventricular systole). Alternatively, synchronization can be accomplished using (1) an arterial waveform from an arterial line in the radial or femoral artery (upstroke of arterial mode is sensed by console), or (2) an external pacemaker, where inflation is timed to occur at the pacing artifact (i.e., pacemaker spike). By repeating this cycle of inflating with a gas during diastole and deflating by withdrawing the gas during systole, the pumping action of the heart is mechanically assisted by (1) reducing systemic afterload, (2) increasing coronary perfusion, and (3) decreasing myocardial oxygen consumption. Moreover, cerebral blood flow is also augmented by the combined action of the inflatable member and the expandable member.

Other methods of using the devices of the invention will include measuring a physiologic parameter, and adjusting the expansion of the expandable member based on the measured physiologic parameter. In certain cases, the physiologic parameter is blood pressure measured at a location upstream the expandable member and/or downstream the expandable member. In other cases, the physiologic parameter is cerebral blood flow. Still other methods will include deploying an interventional catheter (e.g., PTCA, stent, atherectomy, thrombectomy, ablation, electrophysiology, laser) or diagnostic catheter (e.g., angiography, ultrasound, fiber optics, optical coherence tomography) slideably inserted through the guidewire lumen of the catheter.

In another embodiment, the catheter is designed to achieve a propagated volume displacement toward and away from the heart. The catheter comprises an elongate tubular member having a proximal end, a distal end, and a distal region. A first balloon is attached to the elongate tubular member at the distal region and communicates with a first inflation lumen. The first balloon has an inflation volume of 10-30 cc. A second balloon is also attached to the elongate tubular member at the distal region and located distal the first balloon, and communicates with a second inflation lumen. The second balloon has an inflation volume of 10-30 cc. A third balloon is attached to the elongate tubular member at the distal region and located distal the second balloon, and communicates with a third inflation lumen. The third balloon has an inflation volume of 10-30 cc.

A blood pressure measuring mechanism may be included for measuring blood pressure upstream of the third balloon, between the second and third balloon, between the first and second balloon, and/or downstream to the first balloon. The one or more pressure measuring mechanisms may take the form of either a pressure lumen that communicates with an external blood pressure transducer or a blood pressure transducer mounted on the catheter. During use, the first, second, and third balloons are sequentially inflated during diastole to propagate blood flow retrograde to the coronary and carotid arteries. The third, second, and first balloons are then sequentially deflated during the ejection phase of the left ventricle to propagate blood flow antegrade and mechanically assist the pumping action of the heart.

The catheter may optionally further include a fourth balloon attached to the elongate tubular member at the distal region, that communicates with a fourth inflation lumen. The fourth balloon is located distal the third balloon and has an inflation volume of 10-30 cc. The catheter may optionally include a fifth balloon attached to the elongate tubular member at the distal region, that communicates with a fifth inflation lumen. The fifth balloon is located distal the fourth balloon and has an inflation volume of 10-30 cc. The catheter may further include an additional lumen that extends from the proximal end to the distal region and is adapted to slideably receive and pass a guidewire and/or an interventional catheter.

In use, the distal end of the catheter is advanced into the aorta, and typically is placed so that the first, second, and third balloons are positioned in the descending aorta. The first balloon, the second balloon, and the third balloon are sequentially inflated during diastole to partially or fully obstruct the aorta, thereby propagating blood flow retrograde to the coronary arteries and the carotid arteries. After balloon inflation, the third balloon, the second balloon, and the first balloon are sequentially deflated during the ejection phase of the left ventricle to draw blood flow antegrade. Where optional fourth and fifth balloons are present, these balloons are included in the inflation and deflation sequence.

Here too, the methods will include measuring an electrocardiogram and synchronizing inflation with the R wave of the electrocardiogram, so that maximum inflation occurs at the peak of the T wave (which corresponds approximately with closure of the aortic valve), and deflation is timed to occur just before the next QRS complex of the electrocardiogram (which correlates with ventricular systole). Alternatively, synchronization can be accomplished using (1) an arterial waveform from an arterial line in the radial or femoral artery (upstroke of arterial mode is sensed by console), or (2) an external pacemaker, where inflation is timed to occur at the pacing artifact (i.e., pacemaker spike).

By repeating this cycle of sequentially inflating the balloons with a gas during diastole and sequentially deflating the balloons by withdrawing the gas during systole, the pumping action of the heart is mechanically assisted by (1) reducing systemic afterload, (2) increasing coronary perfusion, and (3) decreasing myocardial oxygen consumption. Moreover, cerebral blood flow is also augmented by the combined action of the inflatable member and the expandable member.

In still another method for mechanically assisting the pumping action of the heart, a catheter is provided comprising an elongate member having a proximal end and a distal region. The catheter further includes an expandable member attached in the distal region and an inflatable member in the distal region and attached proximal the expandable member. The catheter is equipped with a lumen that communicates with the inflatable member and extends proximally and, where the expandable member is also a balloon, a second lumen that communicates with the expandable member. The catheter is inserted into a subclavian artery, and then the distal end of the catheter is advanced into the aorta. The expandable member is expanded to at least partially obstruct the aorta. The inflatable member is then inflated during diastole and deflated during the ejection phase of the left ventricle. The pumping action of the heart is thereby mechanically assisted in the manner described herein above.

DETAILED DESCRIPTION

Figure 1A:
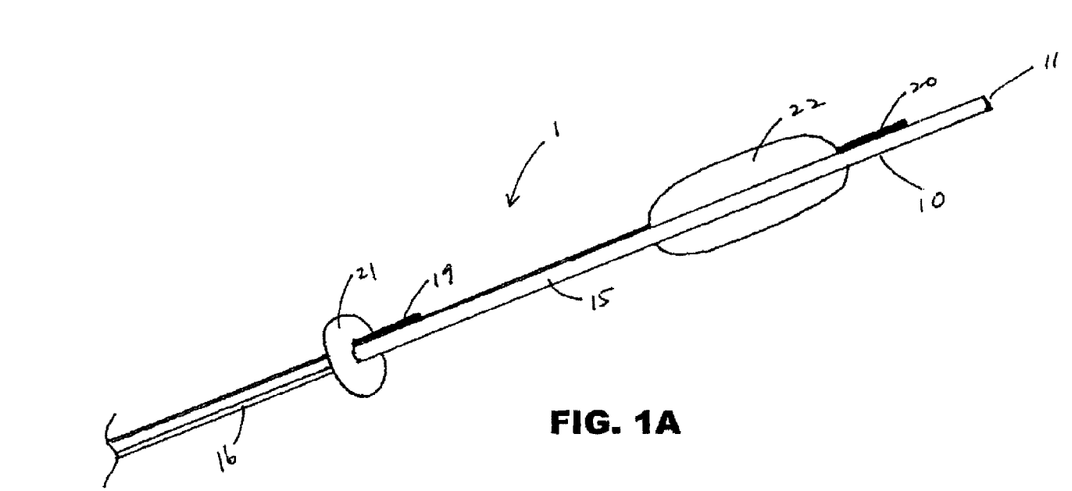
FIG. 1A depicts a distal region of an embodiment of the intraaortic balloon pump catheter according to the present invention.
Figure 1B:
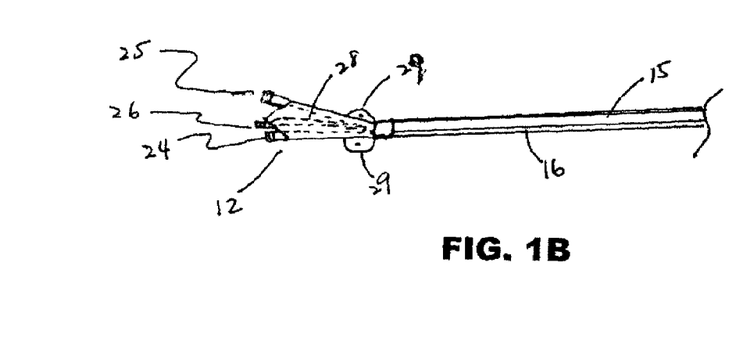
FIG. 1B depicts a proximal region of the catheter of FIG. 1A.

An embodiment of the intraaortic balloon pump catheter having improved volume-displacement efficiency is shown in FIGS. 1A and 1B. Catheter 1 comprises elongate tubular member 10 having lumen 15 extending between distal end 11 and proximal end 12. First balloon 21 is attached to catheter 1 at the distal region. Second balloon 22 (typically made from a thin film of polyurethane because of its strength and antithrombotic properties) is attached to catheter 1 distal to first balloon 21. Lumen 15 of the catheter communicates with balloon 22 for inflation of the second balloon. Similarly, lumen 16 of the catheter communicates with balloon 21 for inflation of the first balloon. Pressure lumen or manometer 19, adapted for measuring blood pressure between balloons 21 and 22, is located distal to balloon 21. Pressure lumen or manometer 20, adapted for measuring blood pressure upstream balloon 22, is located distal balloon 22. At proximal end 12 of catheter 1 as depicted in FIG. 1B, port 24, port 25, and port 26 are housed within catheter hub 28. Port 25 communicates with lumen 15 and is adapted for connecting to a console that synchronizes inflation and deflation of balloon 22 with cardiac cycle and makes automatic adjustments for changes in the heart rate and rhythm. Port 26 is adapted for connecting to a console that allows inflation and deflation of balloon 21 independent of cardiac cycle and balloon 22. Port 24, which communicates with manometers 19 and 20, is adapted for connecting to a blood pressure monitor. Where pressure lumens 19 and 20 are present, these lumens communicate separately and independently with separate and independent ports 24a and 24b, which in turn are connected to external manometers. The proximal end of the catheter also includes suture flanges 29 for securing the catheter in place after insertion.

Figure 2A:
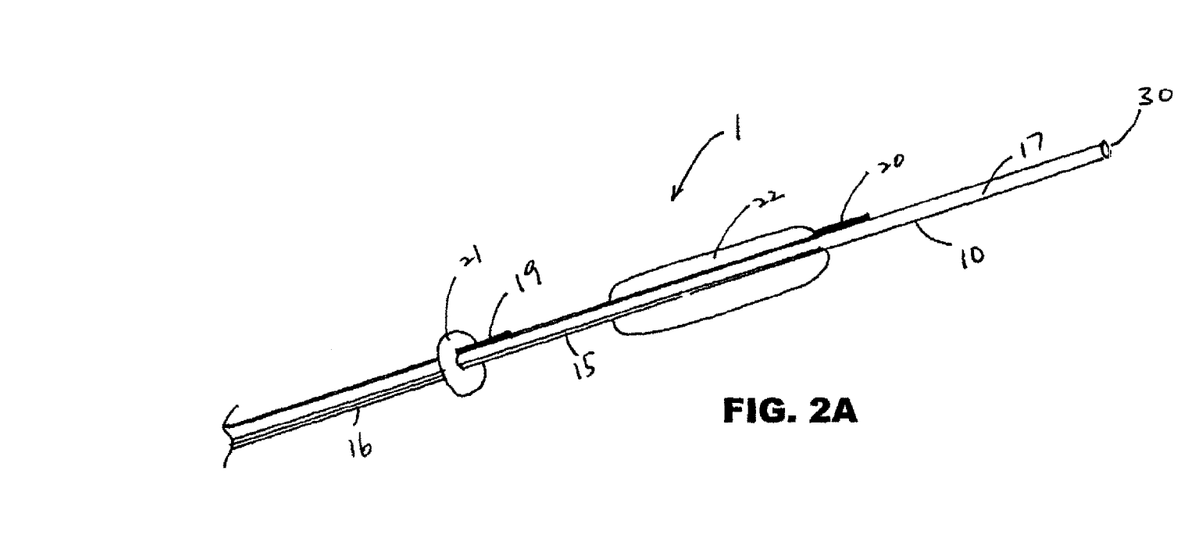
FIG. 2A depicts a distal region of another embodiment of the intraaortic balloon pump catheter having an additional lumen for introducing interventional devices.
Figure 2B:
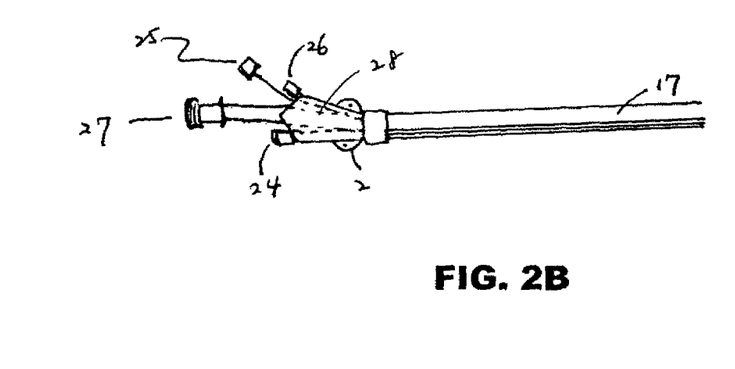
FIG. 2B depicts a proximal region of the catheter of FIG. 2A.

Another embodiment of the intraaortic balloon pump catheter having a third lumen adapted for insertion of interventional catheters is shown in FIGS. 2A and 2B. Lumen 17 communicates proximally with port 27 and distally with port 30. Interventional catheters, such as an angioplasty catheter, an angiography catheter, a stent deployment catheter, a thrombectomy catheter, an embolectomy catheter, an electrophysiology study catheter, a blood filter, or an intravascular ultrasound catheter, may be introduced through port 27, lumen 17, and port 30 to perform desired interventional procedures upstream of catheter 1 when placed in the descending aorta.

Figures 3, 3A:
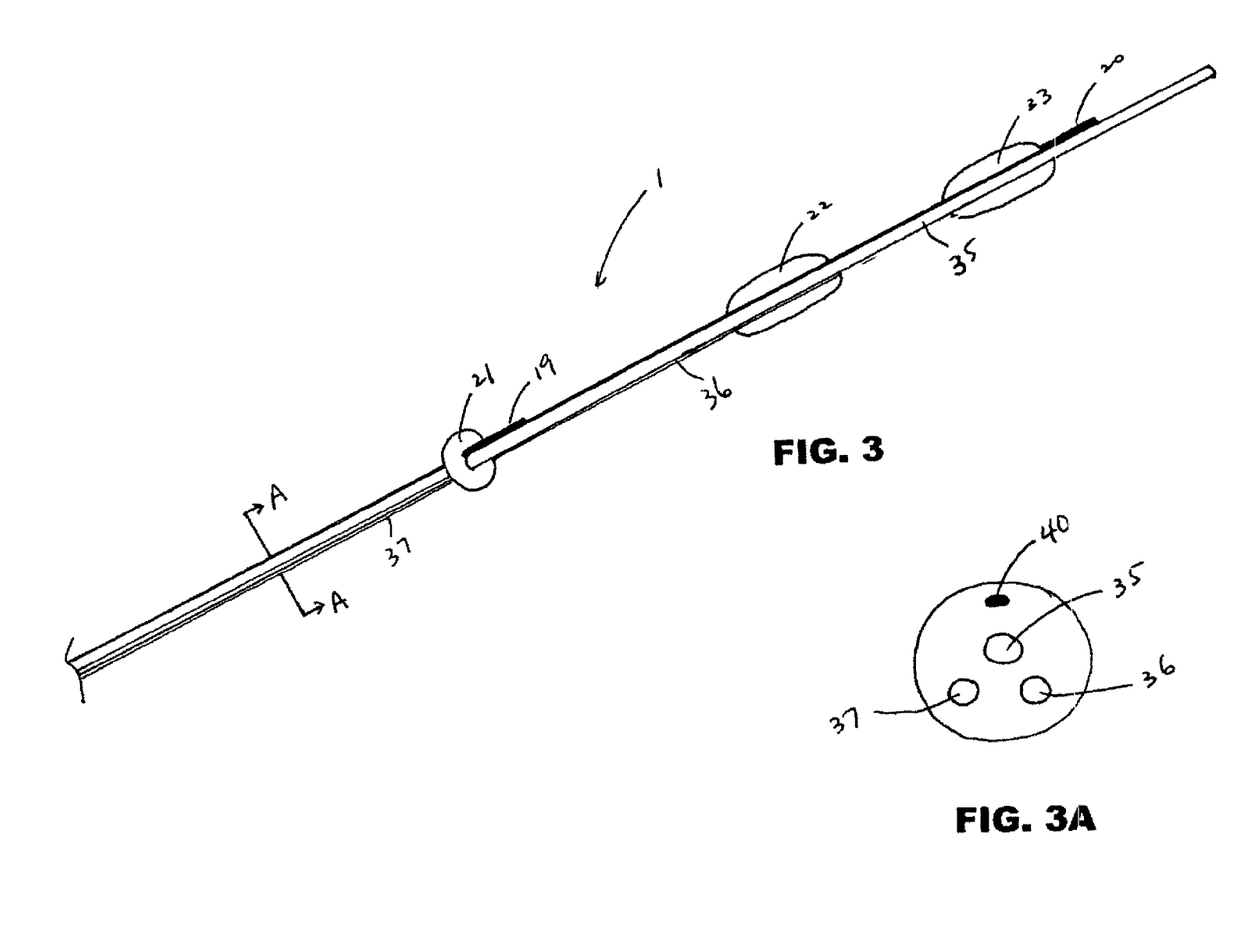
FIG. 3 depicts a distal region of another embodiment of the intraaortic balloon pump catheter having three inflatable balloons.
FIG. 3A depicts a cross-sectional view of the catheter of FIG. 3 through section line A-A.

A further embodiment of an intraaortic balloon pump catheter is depicted in FIG. 3. Catheter 1 includes first balloon 21 that communicates with inflation lumen 37. Second balloon 22 is mounted distal balloon 21, and communicates with inflation lumen 36. Third balloon 33 is mounted distal second balloon 22, and communicates with inflation lumen 35. Pressure lumen or manometer 19 is mounted distal first balloon 21 for obtaining aortic blood pressure readings upstream balloon 21. Second pressure lumen or second manometer 20 is mounted distal third balloon 33 for obtaining aortic blood pressure readings upstream balloon 33. A cross section through section line A-A of catheter 1 is shown in FIG. 3A. Inflation lumens 35, 36, and 37 are depicted, as well as pressure lumen or manometer lumen 40. It will be understood that where the catheter includes pressure lumens 19 and 20 each communicating at a proximal end with an external manometer, pressure lumen 40 will actually be comprised of two separate and independent pressure lumens 40a and 40b (see FIG. 4A), each of which communicates with a separate and independent proximal port 24a and 24b, each of which is connected to a separate and independent external manometer.

Figures 4, 4A:
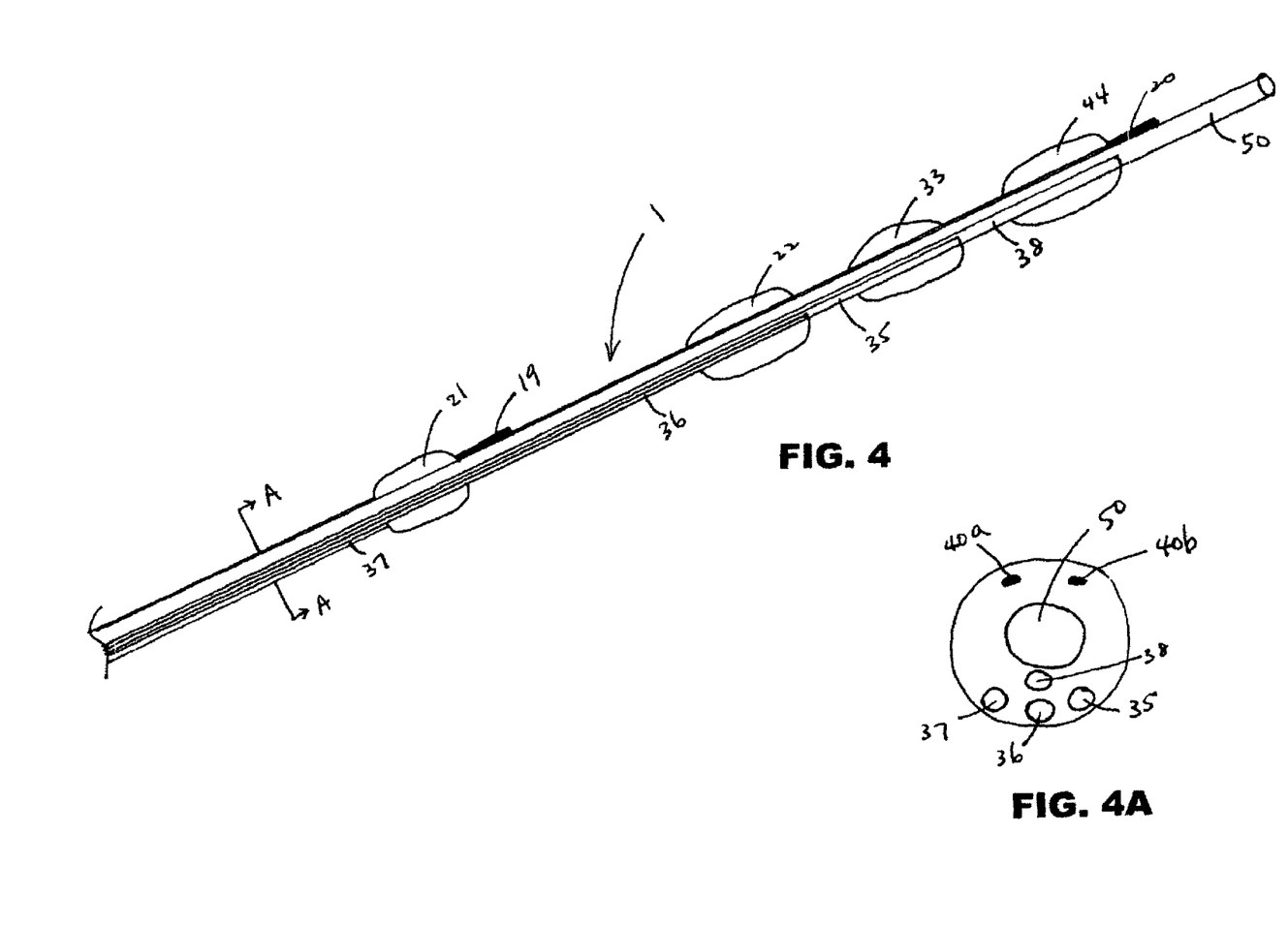
FIG. 4 depicts a distal region of another embodiment of the intraaortic balloon pump catheter having four inflatable balloons.
FIG. 4A depicts a cross-sectional view of the catheter of FIG. 4 through section line A-A.

In another embodiment, catheter 1 is equipped with four balloons, as shown in FIG. 4. Catheter 1 includes first balloon 21 communicating with inflation lumen 37. Second balloon 22 is mounted distal first balloon 21, and communicates with inflation lumen 36. Third balloon 33 is mounted distal second balloon 22, and communicates with inflation lumen 35. Fourth balloon 44 is mounted distal third balloon 33, and communicates with inflation lumen 38. Pressure lumen or manometer 19 is mounted distal first balloon 21 for obtaining aortic blood pressure readings upstream balloon 21. Second pressure lumen or second manometer 20 is mounted distal fourth balloon 44 for obtaining aortic blood pressure readings upstream balloon 44. A cross section through section line A-A of catheter 1 is shown in FIG. 4A. Inflation lumens 35, 36, 37, and 38 are depicted, as well as pressure lumens 40a and 40b which communicate separately with pressure elements 19 and 20, respectively. Catheter 1 of FIG. 4 also includes lumen 50 shown in FIG. 4A for passing an interventional or diagnostic catheter to a location (coronary arteries, carotid arteries, mitral valve, aortic valve, or other arteries of the bead and neck) upstream catheter 1.

Figure 5A:
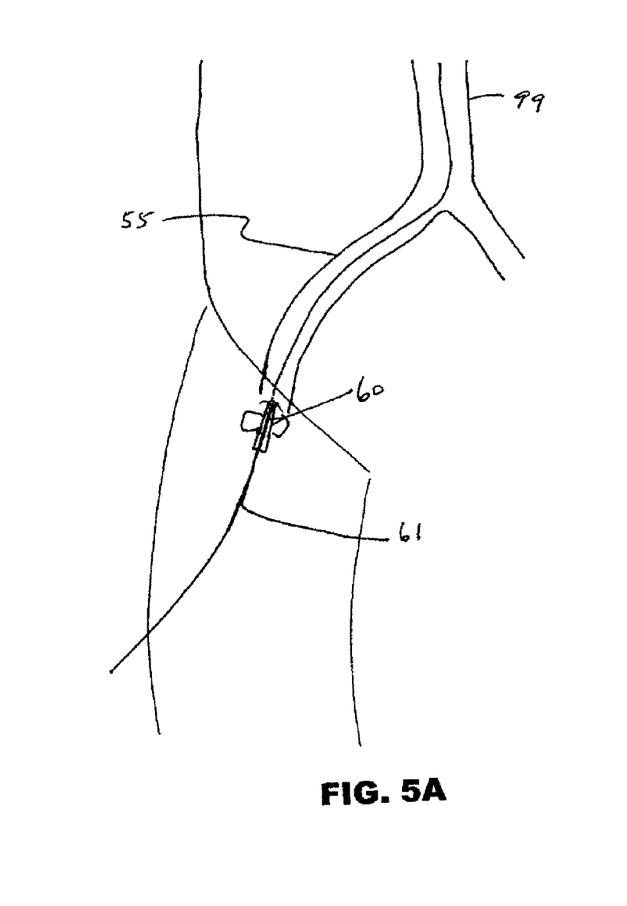
FIG. 5A depicts insertion of a guidewire through a needle in the right femoral artery in preparation for introduction of an intraaortic balloon pump catheter.
Figure 5B:
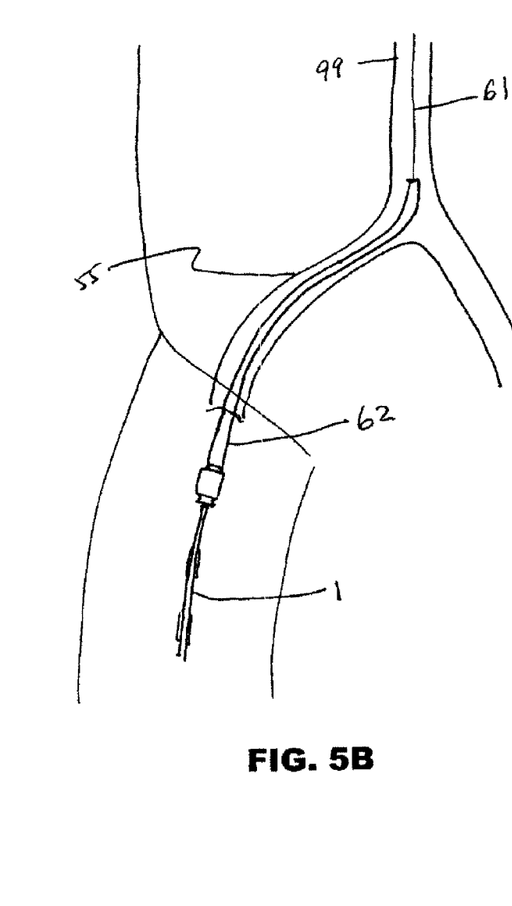
FIG. 5B depicts insertion of an intraaortic balloon pump catheter through a dilator-introducer in the right femoral artery.

In use, the catheter is deployed though a femoral artery as shown in FIGS. 5A and 5B. After the right groin is sterile prepared, needle 60 is inserted into right femoral artery 55. Guidewire 61 is inserted through needle 60, and is advanced into right femoral artery 55 and then into aorta 99 where it will be positioned in the thoracic aorta. Needle 60 is then removed and dilator/introducer 62 is inserted over guidewire 61 as shown in FIG. 5B, or alternatively, catheter 1 may be inserted over the guidewire without the use of a dilator/introducer 62. Catheter 1 is then advanced over guidewire 61 and through introducer/dilator 62. The catheter is then advanced under fluoroscopy (to visualize one or more radio-opaque markers mounted on the distal region of catheter 1) until the distal end of the catheter is positioned approximately 2 centimeters downstream of the orifice of the left subclavian artery (98 in FIG. 6A). The guidewire may then be withdrawn from the patient, or alternatively the guidewire may be left in place to be used during a later interventional catheterization.

Figure 6A:
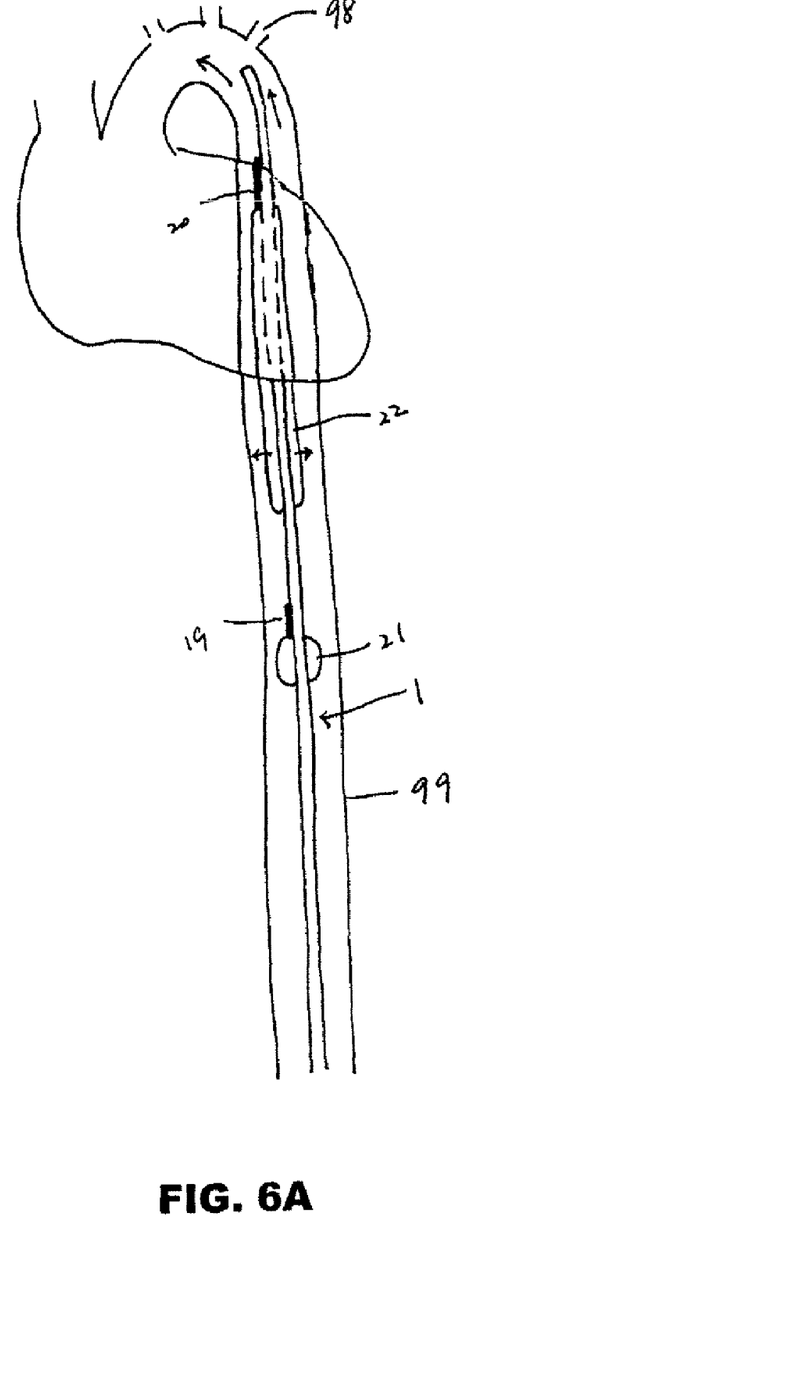
FIG. 6A depicts inflation of the balloons of the intraaortic balloon pump catheter of FIG. 1A in the aorta.
Figure 6B:
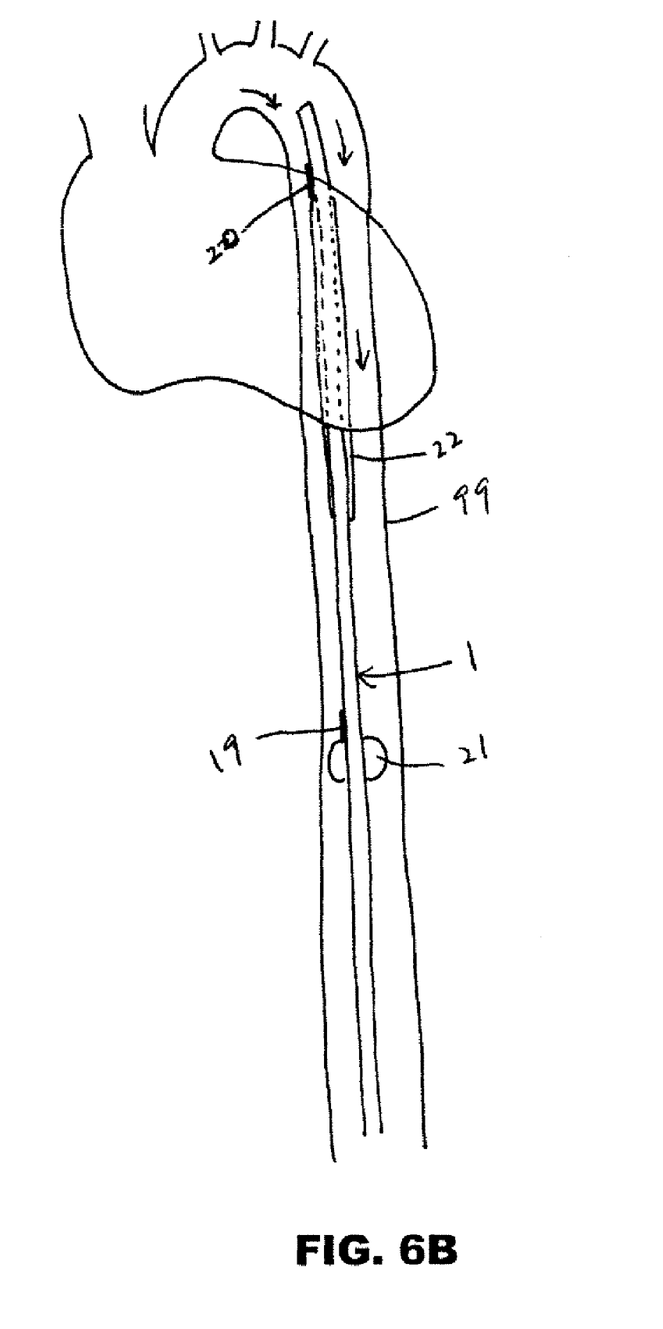
FIG. 6B depicts deflation of a balloon of the catheter in FIG. 6A to reduce cardiac afterload.

With the catheter now in place as shown in FIG. 6A, the inflation lumen for balloon 22 is connected proximally to a console that synchronizes inflation and deflation with the cardiac cycle and makes automatic adjustment for changes in heart rate and rhythm. Balloon 21 is then expanded to partially or fully obstruct aorta 99. Balloon 21 will be maintained expanded to 60% or more, 70% or more, 80% or more, 90% or luminal obstruction to achieve coarctation and enhancement of cerebral blood flow that is highly advantageous in a patient suffering a cerebral vascular accident. In this regard, Barbut et al., U.S. application Ser. No. 09/841,929, filed Apr. 24, 2001, is incorporated herein by reference in its entirety as if fully set forth herein. Maintenance of balloon 21 in an expanded state also enhances the efficiency of counterpulsation balloon 22. Balloon 22 is then expanded during diastole (FIG. 6A) to enhance coronary perfusion, and deflated during systole (FIG. 6B) to reduce afterload in the manner described herein above. Throughout the procedure, blood pressure upstream second balloon 22 may be monitored by readings from pressure lumen or manometer 20 and blood pressure between second balloon 22 and first balloon 21 may be monitored by readings from pressure lumen or manometer 19.

In using the intraaortic balloon pump catheter of FIG. 4, placement in the thoracic aorta is accomplished as described herein above, as shown in FIGS. 7A through 7E. The lumens of balloons 22, 33, and 44 are connected proximally to a console that synchronizes inflation and deflation with the cardiac cycle and makes automatic adjustment for changes in heart rate and rhythm. Balloon 21 is then expanded to partially or fully obstruct aorta 99. Balloon 21 will be maintained expanded to 60% or more, 70% or more, 80% or more, 90% or more luminal obstruction to achieve coarctation and enhancement of cerebral blood flow which is highly advantageous in a patient suffering a cerebral vascular accident. Maintenance of balloon 21 in an expanded state also enhances the efficiency of counterpulsation balloons 22, 33, and 44.

Figure 7A:
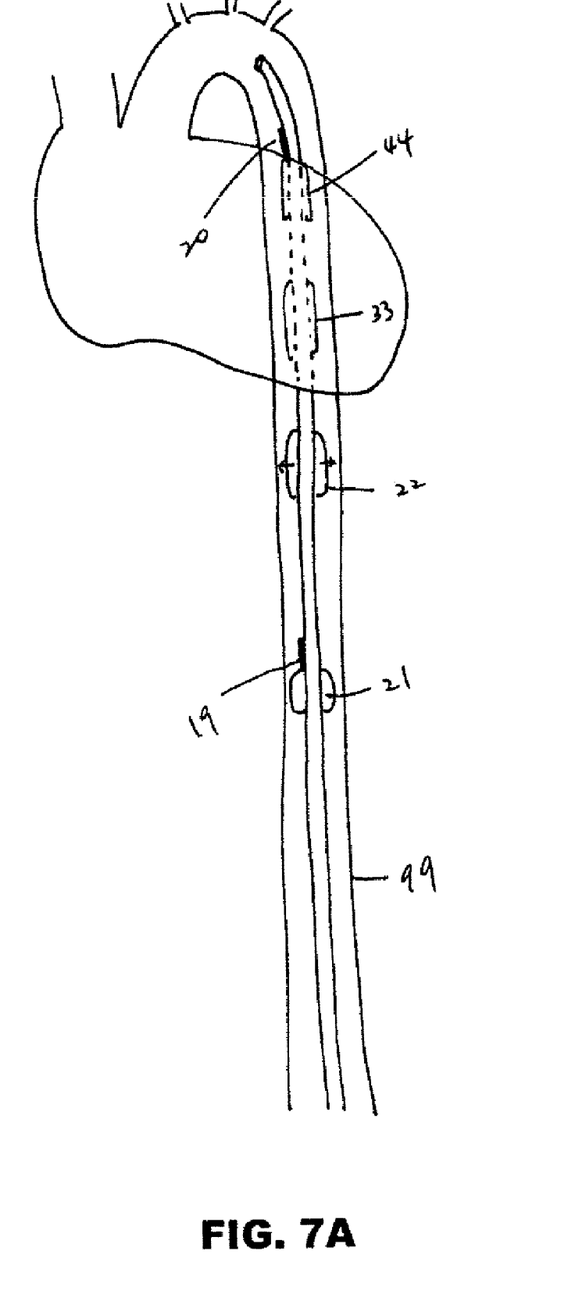
FIG. 7A depicts inflation of balloons of the intraaortic balloon pump catheter of FIG. 4 in the aorta.
Figure 7B:
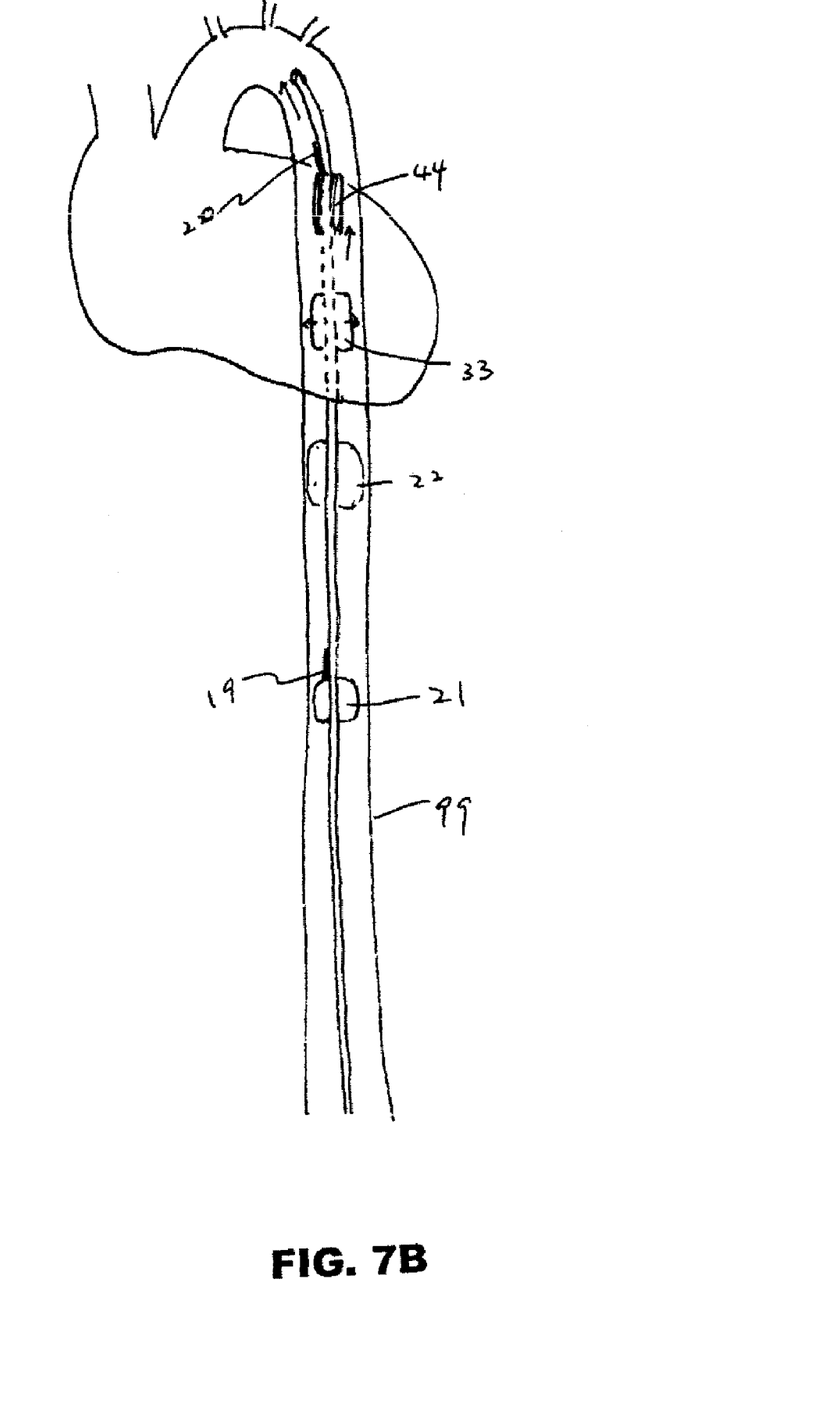
FIG. 7B depicts inflation of another balloon of the catheter of FIG. 7A.
Figure 7C:
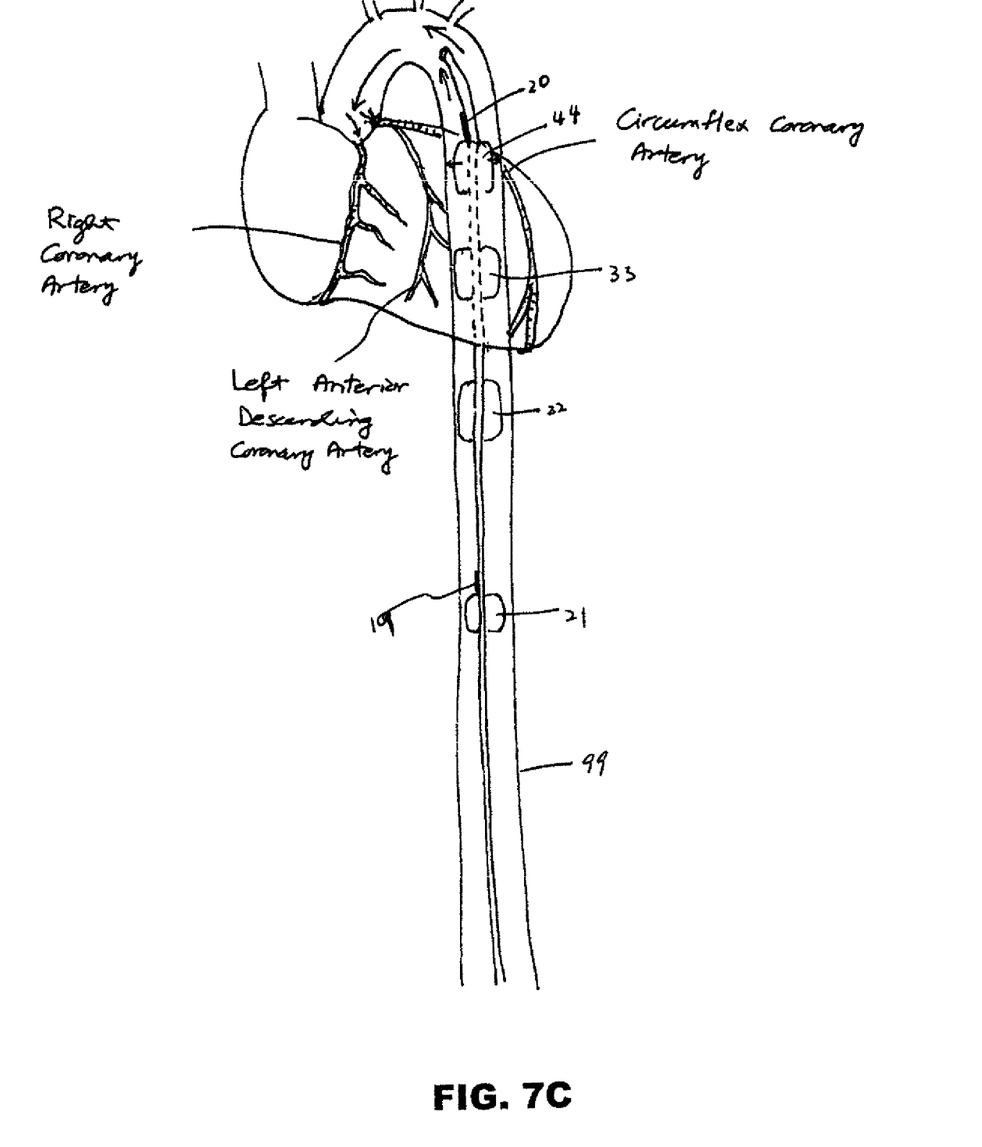
FIG. 7C depicts inflation of all the balloons of the catheter of FIG. 7B to increase coronary blood flow.
Figure 7D:
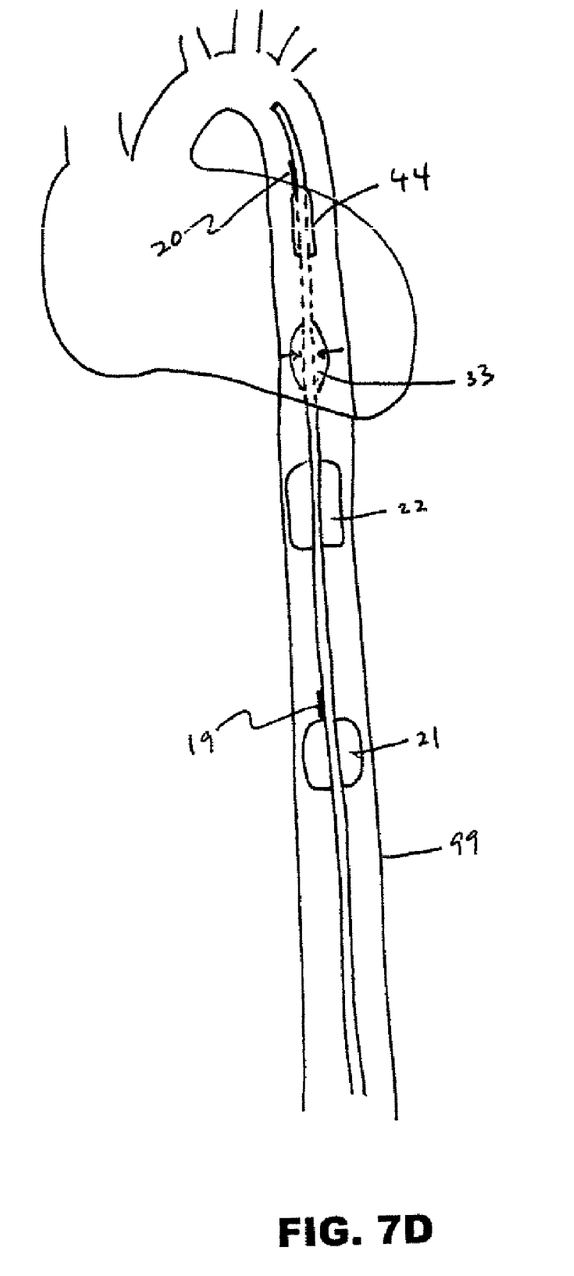
FIG. 7D depicts sequential deflation of balloons in the distal region of the catheter of FIG. 7C to assist in cardiac afterload reduction.
Figure 7E:
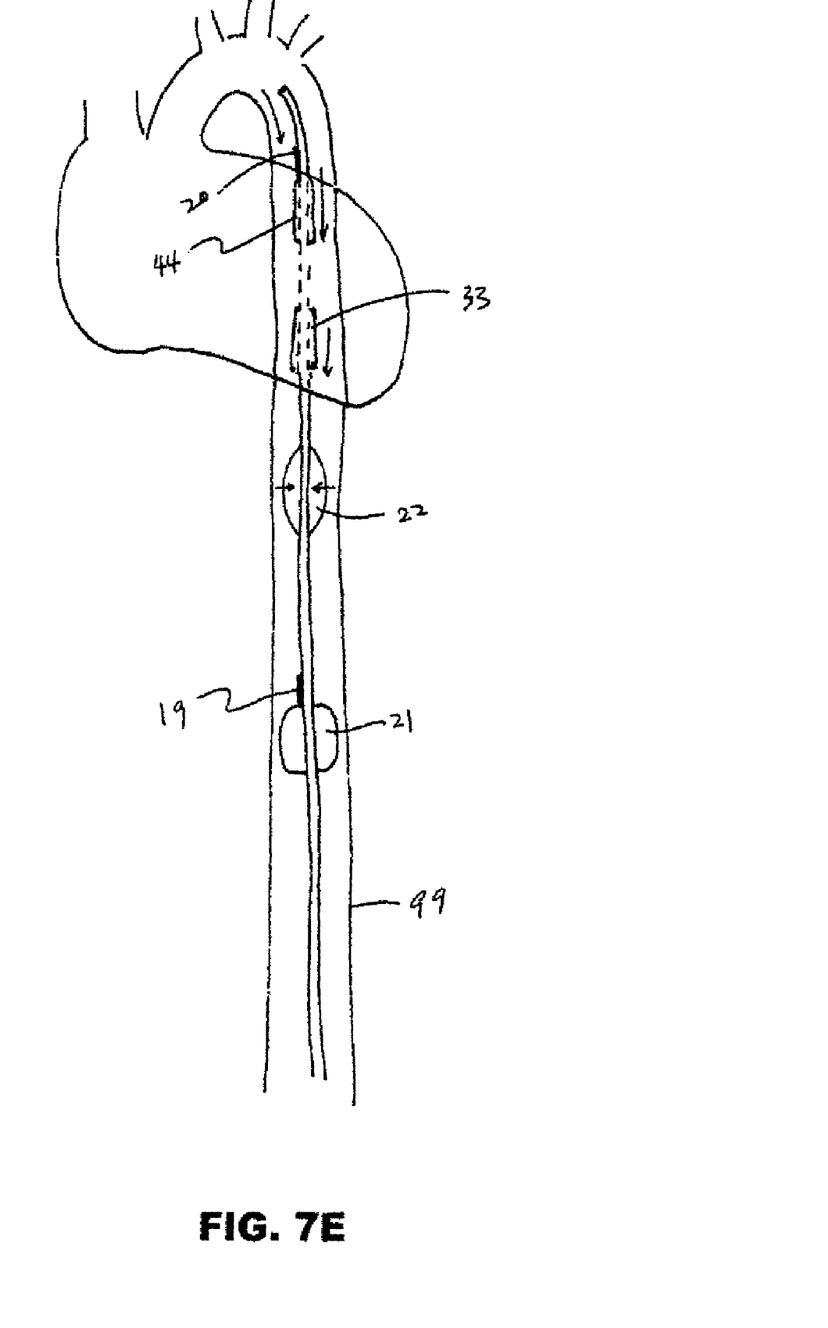
FIG. 7E depicts deflation of the balloons in the distal region of the catheter of FIG. 7C to assist in cardiac afterload reduction.

As shown in FIG. 7A, the inflation cycle begins with counterpulsation balloon 22 during diastole. Volume displacement occurs predominantly upstream because balloon 21 blocks volume displacement downstream. The expansion of balloon 22 is followed immediately by expansion of balloon 33 as shown in FIG. 7B. Again volume displacement occurs predominantly upstream, enhancing coronary perfusion and myocardial oxygenation. Expansion of balloon 33 is followed immediately by expansion of balloon 44 as shown in FIG. 7C. Once again volume displacement occurs predominantly upstream. The diastolic phase of the cardiac cycle is followed by the systolic phase of the cardiac cycle in which blood is ejected from the left ventricle following left ventricular contraction. During this phase of the cardiac cycle, the balloons of catheter 1 are deflated to cause in reduction of left ventricular afterload and systemic vascular resistance. As shown in FIG. 7D, balloon 44 is first deflated to cause downstream volume reduction. Deflation of balloon 44 is followed immediately by deflation of balloon 33. Volume reduction again draws blood from the left ventricle downstream. Deflation of balloon 33 is followed immediately by deflation of balloon 22 as shown in FIG. 7E. The sequential deflation of balloon 44, 33, and 22 is accomplished while balloon 21 is maintained in an expanded state so that volume reduction pulls blood downstream from the left ventricle, not upstream from the peripheral vasculature.

While intraaortic balloon pumping is being conducted using any of the devices described herein, it may be desirable to advance an interventional therapeutic or diagnostic catheter through a lumen of catheter 1 and beyond the distal tip in order to access a coronary obstruction, a diseased heart valve, a perforated septum, a ventricular thrombus, a stenosed carotid artery, arrythmiogenic myocardial tissue, and other lesions affecting the arteries of the head and neck.

The catheters in accordance with the devices described herein will typically have a length between approximately 75-150 cm, preferably approximately 80-110 cm. Balloon inflation volume will typically be approximately 10-40 cc for each balloon, preferably approximately 20-25 cc. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A method for mechanically assisting the pumping action of the heart, comprising the steps of:
    providing a catheter comprising an elongate member having a proximal end, a distal region, the catheter further comprising an expandable member attached in the distal region and an inflatable member in the distal region and attached distal the expandable member, the catheter further comprising a lumen that communicates with the inflatable member and extends proximally;
    advancing the distal end of the catheter into the aorta;
    expanding and maintaining the expandable member during systole and diastole to at least partially obstruct the aorta;
    inflating the inflatable member during diastole; and
    deflating the inflatable member during the ejection phase of the left ventricle while expansion of the expandable member is maintained, wherein the pumping action of the heart is mechanically assisted.

2. The method of claim 1, further comprising the steps of repeating the steps of inflating the inflatable member and deflating the inflatable member.

3. The method of claim 1, wherein the catheter is placed so that the inflatable member and the expandable member are positioned in the descending aorta.

4. The method of claim 1, wherein the expandable member is a balloon.

5. The method of claim 1, wherein the expandable member is expanded to fully obstruct the aorta.

6. The method of claim 1, wherein the expandable member is expanded to partially obstruct the aorta.

7. The method of claim 1, wherein the expandable member is expanded to cause an 80 percent obstruction of the aortic lumen.

8. The method of claim 1, further comprising the steps of measuring an electrocardiogram and synchronizing inflation with the R wave of the electrocardiogram, so that maximum inflation occurs at the peak of the T wave, and deflation is timed to occur just before the next QRS complex of the electrocardiogram.

9. The method of claim 1, further comprising the step of measuring a physiologic parameter and adjusting the expansion of the expandable member based on the measured physiologic parameter.

10. The method of claim 9, wherein the physiologic parameter is blood pressure measured at a location upstream the expandable member and/or downstream the expandable member.

11. The method of claim 9, wherein the physiologic parameter is cerebral flood flow.

12. The method of claim 1, wherein cerebral blood flow is augmented by the combined action of the inflatable member and the expandable member.

13. The method of claim 1, further comprising the step of inserting the catheter into a femoral artery before advancing the distal end of the catheter into the aorta.

14. The method of claim 1, wherein the catheter further comprises a second expandable member attached in the distal region proximal the expandable member, and wherein the method further comprises the step of expanding the second expandable member to at least partially obstruct the aorta.

* * * * *